United States Patent

Ikushima

(10) Patent No.: US 9,186,667 B2
(45) Date of Patent: Nov. 17, 2015

(54) DISCHARGE DEVICE AND LIQUID DISPENSING DEVICE, AND METHOD FOR DISPENSING LIQUID

(75) Inventor: Kazumasa Ikushima, Mitaka (JP)

(73) Assignee: MUSASHI ENGINEERING, INC., Tokyo (JP)

(*) Notice: Subject to any disclaimer, the term of this patent is extended or adjusted under 35 U.S.C. 154(b) by 248 days.

(21) Appl. No.: 13/638,718

(22) PCT Filed: Mar. 24, 2011

(86) PCT No.: PCT/JP2011/057107
§ 371 (c)(1),
(2), (4) Date: Jan. 11, 2013

(87) PCT Pub. No.: WO2011/122425
PCT Pub. Date: Oct. 6, 2011

(65) Prior Publication Data
US 2013/0108521 A1 May 2, 2013

(30) Foreign Application Priority Data
Mar. 30, 2010 (JP) .................................. 2010-078176

(51) Int. Cl.
*B01L 3/00* (2006.01)
*B01L 3/02* (2006.01)
*G01N 35/10* (2006.01)

(52) U.S. Cl.
CPC .............. *B01L 3/0293* (2013.01); *B01L 3/0265* (2013.01); *G01N 35/10* (2013.01);
(Continued)

(58) Field of Classification Search
CPC .............. G01N 2015/0288; G01N 2015/1081; G01N 2015/149; B01L 2200/0652
USPC ........................................................ 422/509
See application file for complete search history.

(56) References Cited

U.S. PATENT DOCUMENTS 6,309,600 B1* 10/2001 Hunter ............................ 422/66
2005/0112541 A1* 5/2005 Durack et al. .................... 435/2
(Continued)

FOREIGN PATENT DOCUMENTS

JP   62-182665 A   8/1987
JP   9-43251 A   2/1997
(Continued)

OTHER PUBLICATIONS

International Search Report of PCT/JP2011/057107, mailing date of May 10, 2011.

Primary Examiner — Jill Warden
Assistant Examiner — Brittany Fisher
(74) Attorney, Agent, or Firm — Westerman, Hattori, Daniels & Adrian, LLP

(57) ABSTRACT

The discharge device includes a nozzle unit, a storage unit for supplying a pressure transmission medium under regulated pressure to the nozzle unit side, a pressurization unit for supplying a pressurized gas under regulated pressure to the storage unit side, a pump mechanism, a branch unit for communicating the nozzle unit, the storage unit, and the pump mechanism with each other, a discharge valve for establishing or blocking communication between the branch unit and the nozzle unit, and a supply valve for establishing or blocking communication between the branch unit and the storage unit. In a state of the discharge valve being closed and the supply valve being opened, the pressurized gas under pressure regulated by the pressurization unit is supplied to the storage unit side and the pressure transmission medium in liquid phase under pressure regulated by the storage unit is supplied to the supply valve side.

14 Claims, 10 Drawing Sheets

(52) U.S. Cl.
CPC .... G01N 35/1004 (2013.01); *B01L 2200/0673* (2013.01); *B01L 2400/0478* (2013.01); *B01L 2400/0487* (2013.01); *B01L 2400/0633* (2013.01); *G01N 2035/1041* (2013.01)

(56) References Cited

U.S. PATENT DOCUMENTS

2007/0151616 A1* 7/2007 Znamensky et al. .......... 137/883
2009/0196793 A1* 8/2009 Omuro et al. .................. 422/64

FOREIGN PATENT DOCUMENTS

| JP | 10-96735 A | 4/1998 |
| JP | 2004-061153 A | 2/2004 |
| JP | 2005-257491 A | 9/2005 |
| JP | 2006-284426 A | 10/2006 |
| JP | 2006-308374 A | 11/2006 |
| JP | 2007-278978 A | 10/2007 |

* cited by examiner

DISCHARGE DEVICE AND LIQUID DISPENSING DEVICE, AND METHOD FOR DISPENSING LIQUID

TECHNICAL FIELD

The present invention relates to a technique for sucking a discharge liquid through one nozzle and fly-discharging the discharge liquid, having been sucked at a time, in units of very small amounts plural time in a non-contact manner. More particularly, the present invention relates to a desktop liquid dispensing device and a liquid dispensing method for fly-discharging plural types of discharge liquids in units of very small amounts, i.e., several tens µL (micro-liter) or less, or extremely very small amounts, i.e., several tens nL (nano-liter) or less, through a single nozzle with the action of pressure by employing, as a pressure transmission medium, a liquid different from the discharge liquids.

BACKGROUND ART

In the fields of biology, chemistry, and medical care, the so-called dispensing device is used to dispense a liquid sample and a liquid reagent into containers, such as test tubes or a microplate, in units of very small amounts for the purpose of analysis and inspection. That dispensing device receives attention particularly in use of dispensing a large number of samples, reagents, etc. for analysis of genetic information of animals and plants, screening in creation of medicines, and examination of specimens, e.g., bloods and viruses, in medical care. The reason is that the dispensing device can quickly and accurately perform a lot of operations, which are difficult for a person to manually perform using a pipette, for example. Because the dispensing is performed in many uses as described above, a discharge amount of one droplet is required to be very small (e.g., order of µL (micro-liter) to nL (nano-liter)) and the dispensing device is also required to discharge a very small amount of liquid with high accuracy in order to effectively utilize the samples that are generally expensive or rare. Further, various kinds of analysis and inspections are often performed together from the viewpoint of efficiently progressing a lot of operations. To that end, it is also required for one dispensing device to discharge plural types of liquids.

In general, the dispensing device mainly includes a discharge unit constituted by, e.g., a pump for extracting, from a container storing a liquid sample or a liquid reagent, the sample or the reagent, a nozzle through which the extracted sample or reagent is discharged, and pipes for interconnecting the pump and the nozzle, a driving unit serving as a mechanism to relatively move the nozzle and a container as a dispensing target, and a control unit for controlling operations of individual components including the pump, the driving unit, etc. Among those units, an especially important one is the discharge unit that directly handles the liquid sample and the liquid reagent.

Although there are various types of discharge units, they are mainly grouped into two types depending on a direction in which the sample or the reagent is supplied. In one type, the sample or the reagent is supplied from an opposite end to a discharge port (nozzle). In the other type, the sample or the reagent is supplied from the same end as the discharge port (nozzle), i.e., the sample or the reagent is sucked through the discharge port (nozzle) and then discharged through the discharge port (nozzle). In particular, when the sample or the reagent is expensive or rare and can be prepared just in such a small amount that the pump, the pipes, etc. cannot be filled with the sample or the reagent in amount necessary for operations, or when there are many types of samples or reagents to be discharged and operations of removing the samples or the reagents filled into the pump, the pipes, etc. and cleaning them are troublesome, the other type of the dispensing device is often used in which the sample or the reagent is supplied from the same end as the discharge port (nozzle), i.e., the sample or the reagent is sucked through the discharge port (nozzle) and then discharged through the discharge port (nozzle).

In the dispensing device of the other type described above, for accurate discharge in a very small amount, the sample or the reagent discharged through the discharge port (nozzle) is often discharged in such a manner that the sample or the reagent is departed from a tip end of the discharge port (nozzle) before reaching a target, thus causing the sample or the reagent to fly toward the target. In this specification, such discharge is called "fly-discharge" or "non-contact discharge".

Patent Document 1 states that a dispensing device for discharging a liquid with reciprocal motions of a piston has a problem of being not suitable for a dispensing operation, which requires accuracy of less than several µL, due to the occurrence of a dispensing error. To cope with such a problem, Patent Document 1 proposes a dispensing device in which a liquid can be discharged in an amount of about 200 µL at certain accuracy by discharging the liquid with application of positive pressure from a pressurized gas supply source (or application of positive pressure from a cylinder device in a combined manner). In the device of Patent Document 1, however, because gas (air) is used as a pressure transmission medium, a problem may arise in response and accuracy due to compressibility of the gas (air). For that reason, a dispensing device using a liquid as a pressure transmission medium is also proposed as disclosed in Patent Document 2. Among dispensing devices each using a liquid as a pressure transmission medium, there are dispensing devices, as disclosed in Patent Documents 3 and 4, in which, instead of directly discharging the sample or the reagent with the action of a piston (plunger) of a pump, a valve is disposed midway a piping line and the sample or the reagent is discharged with opening and closing of the valve while the sample or the reagent is previously pressurized by the pump or another pressurizing means.

PRIOR ART DOCUMENTS

Patent Documents

Patent Document 1: Japanese Patent Laid-Open Publication No. S62-182665
Patent Document 2: Japanese Patent Laid-Open Publication No. H10-96735
Patent Document 3: Japanese Patent Laid-Open Publication No. 2006-308374
Patent Document 4: Japanese Patent Laid-Open Publication No. 2006-284426

SUMMARY OF THE INVENTION

Problems to be Solved by the Invention

When the "fly-discharge" or the "non-contact discharge" is performed by discharging one droplet in a very small amount (e.g., several tens µL or less), particularly (e.g., several tens nL or less), the device constructed to discharge the droplet with the action of the piston (plunger) cannot sufficiently accelerate the droplet because of a short stroke distance and cannot give the droplet with a force (pressure) enough to fly it.

On the other hand, when a liquid transmission medium (system liquid) is pressurized by the pump like the dispensing device described in Patent Document 3, there is a problem that a mechanism for holding a certain pressure is complicated due to the necessity of providing an additional device, such as a sensor, and of performing feedback control of pressure change of the liquid (see, e.g., paragraph [0030] in Patent Document 3). Another problem is that, because the pump is always held in an operating state during continuous discharge of the liquid, a load exerted on the pump is increased and the service life of the pump is shortened.

When the liquid transmission medium is directly pressurized using the gas like the dispensing device described in Patent Document 4, there is a problem that the action of gas pressurization may be directly transmitted to the sample. In more detail, problems may occur with an influence of the water head difference due to reduction of the liquid transmission medium inside a buffer tank, an influence of compressibility of the gas, and an influence of pressure variation (pulsation) in a gas pressurization source. Those influences degrade dispensing accuracy for the reason that the pressure transmission medium is supplied to the valve under pressure that is in a poor state not only in response attributable to the water head difference and the compressibility of the gas, but also in stability attributable to the pressure variation (pulsation) in the gas pressurization source.

A still another problem to be solved when different types of samples or reagents are discharged is mixing (contamination) of the samples and/or the reagents in the nozzle. Patent Document 2 discloses an arrangement for supplying a cleaning liquid to flow through a flow passage, but such an arrangement still accompanies with a risk that the cleaning liquid may remain in a nozzle tip portion (particularly on an outer surface of the nozzle tip portion) and the samples and/or the reagents may mix with each other when the samples and/or the reagents are sucked. Therefore, a dispensing device is demanded which can realize a series of cleaning operations including treatment of wastes, supply of the cleaning liquid, and drying of the nozzle. In particular, a desktop dispensing device capable of realizing such a series of cleaning operations is demanded.

Accordingly, an object of the present invention is to provide a discharge device, a liquid dispensing device, and a liquid dispensing method, which have succeeded in solving the above-described problems.

Means for Solving the Problems

According to a first aspect of the present invention, there is provided a discharge device for sucking a discharge liquid in an amount corresponding to plural discharges through a discharge port of a nozzle unit having a flow passage, which is filled with a pressure transmission medium, with a gap interposed between the pressure transmission medium and the discharge liquid, and for continuously fly-discharging very small amounts of liquid droplets, the discharge device comprising the nozzle unit having the flow passage that is communicated with the discharge port, a storage unit for supplying the pressure transmission medium in liquid phase under regulated pressure to the nozzle unit side, a pressurization unit for supplying a pressurized gas under regulated pressure to the storage unit side, a pump mechanism communicated with the storage unit and the nozzle unit in a fluid communicating way, a branch unit provided with a branched flow passage communicating the nozzle unit, the storage unit, and the pump mechanism with each other, a discharge valve for establishing or blocking communication between the branch unit and the nozzle unit, a supply valve for establishing or blocking communication between the branch unit and the storage unit, and a control unit, wherein the control unit performs control such that, in a state where the discharge valve is closed and the supply valve is opened, the pressurized gas under pressure regulated by the pressurization unit is supplied to the storage unit side and the pressure transmission medium in liquid phase under pressure regulated by the storage unit is supplied to the supply valve side, and that the discharge valve is then opened and closed at predetermined timings, thereby continuously fly-discharging the very small amounts of liquid droplets.

According to a second aspect of the present invention, in the first aspect, the pressurization unit includes a gas regulator, and the storage unit includes a liquid regulator.

According to a third aspect of the present invention, in the first aspect, the pressurization unit includes a dispense controller.

According to a fourth aspect of the present invention, in any one of the first to third aspects, the branch unit is constituted as a block-like member, and the discharge device includes a head unit that is constituted by arranging the block-like member, the supply valve, the pump mechanism, the discharge valve, and the nozzle unit integrally with one base.

According to a fifth aspect of the present invention, there is provided a liquid dispensing device comprising the discharge device according to any one of the first to fourth aspects, a work table on which a dispensing target container and a discharge liquid container are placed, and an XYZ moving mechanism for moving the nozzle unit and the work table relatively to each other.

According to a sixth aspect of the present invention, in the fifth aspect, the liquid dispensing device according to the fifth aspect further comprises a cleaning unit that includes a draining portion for receiving the liquid discharged from the nozzle unit and a cleaning liquid spring-out port, and a drying unit for causing a suction force to act on a tip portion of the nozzle unit, thereby drying the tip portion of the nozzle unit.

According to a seventh aspect of the present invention, in the fifth or sixth aspect, the liquid dispensing device is a desktop type.

According to an eighth aspect of the present invention, there is provided a liquid dispensing method for continuously discharging a discharge liquid by employing a liquid dispensing device, which comprises a nozzle unit having a flow passage that is communicated with a discharge port, a storage unit for supplying the pressure transmission medium in liquid phase under regulated pressure to the nozzle unit side, a pressurization unit for supplying a pressurized gas under regulated pressure to the storage unit side, a pump mechanism communicated with the storage unit and the nozzle unit in a fluid communicating way, a branch unit provided with a branched flow passage for communicating the nozzle unit, the storage unit, and the pump mechanism with each other, a discharge valve for establishing or blocking communication between the branch unit and the nozzle unit, a supply valve for establishing or blocking communication between the branch unit and the storage unit, a work table on which a dispensing target container and a discharge liquid container are placed, and an XYZ moving mechanism for moving the nozzle unit and the work table relatively to each other, the liquid dispensing method comprising a first step of sucking the discharge liquid in an amount corresponding to plural discharges through the discharge port of the nozzle unit having the flow passage, which is filled with the pressure transmission medium, with a gap interposed between the pressure transmission medium and the discharge liquid, a second step of, in a state where the discharge valve is closed and the supply valve is opened, supplying the pressurized gas under pressure regulated by the pressurization unit to the storage unit side, and supplying the pressure transmission medium in liquid phase under pressure regulated by the storage unit to the supply valve side, and a third step of opening and closing the discharge valve at predetermined timings while moving the nozzle unit and the work table relatively to each other, thereby continuously fly-discharging very small amounts of liquid droplets.

According to a ninth aspect of the present invention, there is provided a liquid dispensing method for continuously discharging plural types of discharge liquids by employing a liquid dispensing device, which comprises a nozzle unit having a flow passage that is communicated with a discharge port, a storage unit for supplying a pressure transmission medium in liquid phase under regulated pressure to the nozzle unit side, a pressurization unit for supplying a pressurized gas under regulated pressure to the storage unit side, a pump mechanism communicated with the storage unit and the nozzle unit in a fluid communicating way, a branch unit provided with a branched flow passage for communicating the nozzle unit, the storage unit, and the pump mechanism with each other, a discharge valve for establishing or blocking communication between the branch unit and the nozzle unit, a supply valve for establishing or blocking communication between the branch unit and the storage unit, a work table on which a dispensing target container and a discharge liquid container are placed, an XYZ moving mechanism for moving the nozzle unit and the work table relatively to each other, a cleaning unit that includes a draining portion for receiving the liquid discharged from the nozzle unit and a cleaning liquid spring-out port, and a drying unit for causing a suction force to act on a tip portion of the nozzle unit, thereby drying the tip portion of the nozzle unit, the liquid dispensing method comprising a first step of, for a first discharge liquid, sucking the discharge liquid in an amount corresponding to plural discharges through the discharge port of the nozzle unit having the flow passage, which is filled with the pressure transmission medium, with a gap interposed between the pressure transmission medium and the discharge liquid, a second step of, in a state where the discharge valve is closed and the supply valve is opened, supplying the pressurized gas under pressure regulated by the pressurization unit to the storage unit side, and supplying the pressure transmission medium in liquid phase under pressure regulated by the storage unit to the supply valve side, a third step of opening and closing the discharge valve at predetermined timings while moving the nozzle unit and the work table relatively to each other, thereby continuously fly-discharging very small amounts of liquid droplets, a fourth step of moving the nozzle unit to the cleaning unit, draining the discharge liquid remaining in the nozzle unit, and cleaning the tip portion of the nozzle unit, a fifth step of moving the nozzle unit to the drying unit and drying the tip portion of the nozzle unit, a sixth step of moving the nozzle unit to the cleaning unit and draining the pressure transmission medium through the discharge port in a state where the supply valve is closed and the discharge valve is opened, and a seventh step of performing the first to third steps for a second discharge liquid.

According to a tenth aspect of the present invention, in the eighth or ninth aspect, an amount of the droplet discharged at a time is 1 μL or less.

According to an eleventh aspect of the present invention, in the tenth aspect, the amount of the droplet discharged at a time is several tens nL or less.

Advantageous Effects of the Invention

With the present invention, since a pressure sensor or the like is not provided and there is no need of feed-backing a measurement value, a mechanism for holding a certain pressure is simplified and control is facilitated.

Further, since the pump is not used for pressurization to discharge the liquid and a pressurization load is not exerted on the pump, the service lives of individual components (particularly the pump and an actuator) are prolonged.

Moreover, since the gas pressure and the liquid pressure are separately adjusted, the action of the gas pressurization is avoided from being directly transmitted to the sample or the reagent, response and stability in application of the pressure are improved and the discharge can be realized with higher accuracy.

Since the nozzle tip portion is dried after the cleaning in addition to cleaning the inside and the outside of the nozzle with the cleaning liquid, contamination can be avoided reliably.

Further, in the arrangement where a unit for performing cleaning and drying, along with treatment of wastes and supply of the cleaning liquid, is disposed within a nozzle movable range, a series of operations from the cleaning to the drying of the nozzle tip portion can be automated. In addition, dispensing operations for plural types of discharge liquids can also be automated.

MODE FOR CARRYING OUT THE INVENTION

One example of a mode for carrying out the present invention will be described below. In the following description, the liquid sample and the liquid reagent are collectively called a discharge liquid.

[Construction]

Figure 1:
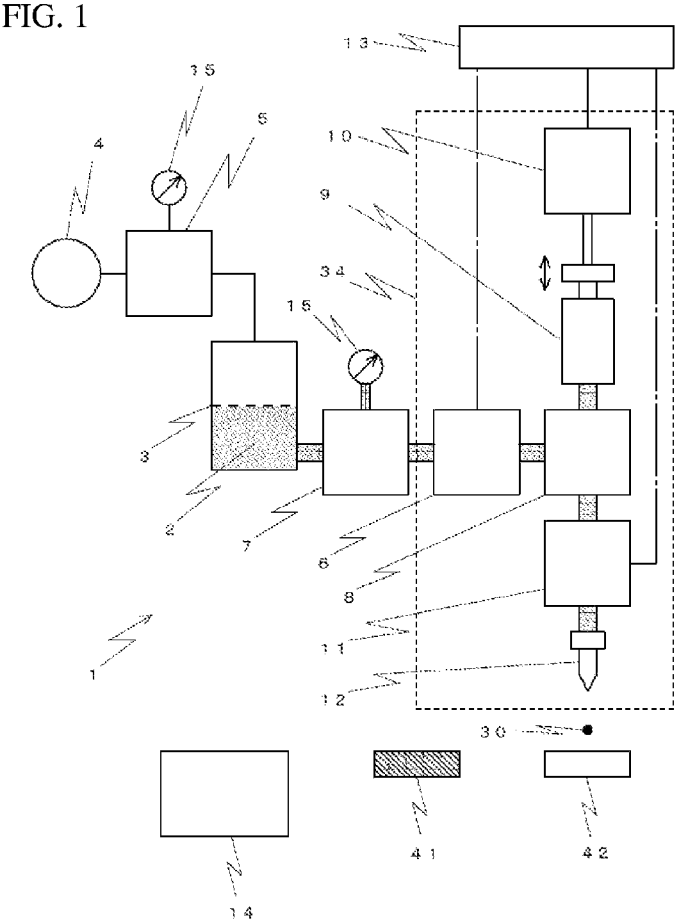
FIG. 1 is an explanatory view to explain a discharge device constituting a dispensing device according to the present invention.

FIG. 1 is an explanatory view to explain a discharge device 1 in a dispensing device according to an embodiment. A head unit 34 (portion surrounded by a dotted line in FIG. 1, described in detail below) constituting the discharge device 1 is movable in the XYZ directions by an XYZ moving mechanism. A liquid is dispensed by moving the head unit 34 and a dispensing target container 42 relatively to each other.

The discharge device 1 in the dispensing device according to the embodiment includes a nozzle unit having a flow passage that is communicated with a discharge port, a storage unit for supplying a pressure transmission medium in liquid phase under regulated pressure to the nozzle unit side, a pressurization unit for supplying a pressurized gas under regulated pressure to the storage unit side, a pump mechanism communicated with the storage unit and the nozzle unit in a fluid communicating way, a branch unit provided with a branched flow passage for communicating the nozzle unit, the storage unit, and the pump mechanism with each other, a discharge valve for establishing or blocking communication between the branch unit and the nozzle unit, a supply valve 6 for establishing or blocking communication between the branch unit and the storage unit, a control unit 13, and a cleaning and drying unit 14 for cleaning and drying an outer surface of a tip portion of a nozzle 12.

The nozzle unit includes a nozzle 12 for sucking a discharge liquid 30, temporarily storing the discharge liquid 30, and then discharging it.

The storage unit includes a storage container 3 for storing a pressure transmission medium 2, and a liquid regulator 7 disposed between the storage container 3 and the supply valve 6 and regulating the pressure transmission medium 2 supplied from the storage container 3 to the desired pressure.

The pressurization unit includes a pressurized gas source 4 connected to the storage container 3 through a gas piping line and supplying a pressurized gas, and a gas regulator 5 disposed between the storage container 3 and the pressurized gas source 4 and regulating the pressurized gas supplied from the pressurized gas source 4 to the desired pressure.

The branch unit includes a branch block 8 for branching the pressure transmission medium 2 supplied from the storage container 3 in a direction toward a pump 9 and in a direction toward the nozzle 12.

The pump mechanism includes the pump 9, which is connected to one of ports of the blanch block 8 and which sucks and drains the discharge liquid 30 with the aid of the pressure transmission medium 2, and an actuator 10 for operating the pump 9.

The control unit 13 controls the actuator 10, the supply valve 6, and the discharge valve 11. Details of the individual components will be described below.

The storage container 3 used in the embodiment is an enclosed container, and it stores the pressure transmission medium 2 therein. The pressure transmission medium 2 is a liquid, and it fills the valves (6, 11), the pump 9, the nozzle 12, and piping lines interconnecting those components such that the action of pressure of the pressure transmission medium 2 is transmitted to the discharge liquid 30 having been sucked into the nozzle 12. The pressure transmission medium 2 serves also as a cleaning liquid. Thus, when the pressure transmission medium 2 is discharged from the nozzle 12 together with the discharge liquid 30, it cleans the inside of the nozzle 12 (particularly in its portion into which the discharge liquid 30 has been sucked). The pressure transmission medium 2 used herein is, e.g., water or a liquid having viscosity comparable to that of water. The pressure transmission medium 2 may contain a surfactant, etc. for better cleaning.

The pressurized gas source 4 for supplying the pressurized gas is connected to an upper portion of the storage container 3 through a gas piping line, and a gas regulator 5 for regulating the pressurized gas to the desired pressure is disposed midway the gas piping line. A known gas regulator can be used as the gas regulator 5. The gas regulator 5 is preferably provided with a gauge (pressure gauge) 15 for confirming a value of the regulated pressure. It is a matter of course that the gauge (pressure gauge) 15 may be of the analog or digital type. The pressure regulation may be performed by turning a thumb associated with the regulator, or by employing the control unit 13 when the regulator is of the electro-pneumatic type. A dispense controller may be used instead of the gas regulator 5. The use of the dispense controller facilitates, for example, setting and change of the pressure value.

The supply valve 6 for starting and stopping supply of the pressure transmission medium 2 to the pump 9 (described later) and the nozzle 12 (described later) is connected to a lower portion of the storage container 3 through a liquid piping line. In the embodiment, a solenoid opening/closing valve is used as the supply valve 12 such that the supply of the pressure transmission medium 2 is started and stopped with the opening and closing of the valve. The opening and closing of the valve is controlled by the control unit 13 (described later).

The liquid regulator 7 is disposed midway the liquid piping line interconnecting the storage container 3 and the supply valve 6. A known liquid regulator can be used as the liquid regulator 7. As in the gas regulator 5, the liquid regulator 7 is also preferably provided with a gauge (pressure gauge) 15 for confirming a value of the regulated pressure. It is a matter of course that the gauge (pressure gauge) 15 may be of the analog or digital type. The pressure regulation may be performed by turning a thumb associated with the regulator, or by employing the control unit 13 when the regulator is of the electro-pneumatic type. By disposing the liquid regulator 7 and the above-described gas regulator 5 in two stages, it is possible to not only regulate and stabilize the pressure of the pressurized gas supplied from the pressurized gas source 4 by the gas regulator 5, but also to regulate and stabilize the pressure of the pressure transmission medium 2, on which the stabilized pressurized gas acts, by the liquid regulator 7. As a result, the influences of, e.g., the water head difference in the storage container 3, the pressure variation (pulsation) in the pressurized gas source 4, and the compressibility of the gas can be removed. Furthermore, with the liquid regulator 7 disposed upstream of an inlet of the supply valve 6, the pressure transmission medium 2 under the regulated and stabilized pressure can be supplied to the supply valve 6 and the other components connected to the outlet side thereof, which are related to the liquid discharge. Hence accuracy and stability in the liquid discharge can be increased.

The branch block 8 is connected to the outlet side of the supply valve 6. The branch block 8 includes a flow passage to branch the pressure transmission medium 2, which is supplied from the storage container 3 through the supply valve 6, in a direction toward the pump 9 (described later) and in a direction toward the nozzle 12 (described later). In the embodiment, the flow passage inside the branch block 8 is formed substantially in a T-shape. Using the branch block 8, which is formed by boring the flow passage in a block-like member, instead of using pipes has the following advantages. First, since the branch block 8 has a thicker wall than the pipe, pressure resistance is increased. Therefore, expansion (or contraction) of the flow passage with application of pressure can be reduced, and durability and accuracy can be increased. Secondly, since the valves (6, 11) and the pump 9 can be directly mounted to the block 8, the number of couplings to be used is minimized. As compared with the case using the couplings, leakage and damage can be reduced, whereby maintainability can be improved. Thirdly, since the length of the flow passage is shortened by forming each portion of the flow passage in a linear shape, response to application of pressure can be improved.

The pump 9 for sucking and draining the discharge liquid 30 with the aid of the pressure transmission medium 2 is communicated with one (on the upper side in FIG. 1) of openings of the branch block 8 in a fluid communicating way. The pump 9 used herein may be, for example, a reciprocating displacement type pump, such as a syringe pump or a piston pump (plunger pump). In the embodiment, the pump 9 is not used for the discharge, and it is used only for sucking and draining the discharge liquid 30. Further, the pump 9 is not used for pressurizing the pressure transmission medium 2. In other words, since the pump 9 does not take part in the discharge operation, fine control for the discharge is not needed in the pump. Further, since the pump 9 does not take part in the pressurization for the liquid discharge, a load attributable to the pressurization is not exerted on the pump 9.

The pump 9 is provided with the actuator 10 for operating the pump 9. Corresponding to the reciprocating displacement type pump, the actuator 10 is constituted, for example, using a combination of a ball screw and a motor (electric motor), or a directly-operated actuator such as an air cylinder. The operation of the pump 9 is controlled by the control unit 13 (described later), which controls the operation of the actuator 10.

When the desktop dispensing device is constructed, the pump 9 and the actuator 10 are preferably arranged above the nozzle 12. The reason is that, with such an arrangement, the head unit 34 (described later) can be constructed in a vertically-long slim shape and a plurality of head units 34 can be easily arranged side by side. In addition, the head unit 34 having a vertically-long shape is more aesthetic in appearance when it is mounted to a Z axis.

The discharge valve 11 for controlling the liquid discharge with opening and closing thereof is communicated with the other opening (on the lower side in FIG. 1) of the branch block 8 in a fluid communicating way. In the embodiment, a small plunger valve is used as the discharge valve 11. Here, another type of valve may also be used. In that case, the valve is preferably capable of opening and closing at a high speed. The liquid discharge is performed by opening and closing the discharge valve 11 at a high speed. The opening and closing of the discharge valve 11 is performed by the control unit 13 (described later).

The nozzle 12 is communicated in a fluid communicating way with an opening of the discharge valve 11 on the side opposite to the opening thereof, which is connected to the branch block 8. The nozzle 12 serves to suck the discharge liquid 30 from a discharge liquid container 41, stores the discharge liquid 30 temporarily, and then discharges it into a dispensing target container 42. In the embodiment, even when different types of discharge liquids are to be dispensed, those discharge liquids can be discharged through one nozzle 12 by cleaning the nozzle 12 for each dispensing (discharge) operation without replacing the nozzle 12. A tip portion of the nozzle 12 is preferably coated with a water repellent material. Examples of the water repellent material include a fluorine-based resin and a silicone-based resin. Because of the tip portion of the nozzle 12 being coated with the water repellent material, it is possible to avoid the discharge liquid 30 and the cleaning liquid 2 from remaining attached to the outer surface of the nozzle 12 after the suction of the discharge liquid 30 and the cleaning, and to prevent undesired dripping and mixing.

The distance of a flow passage extending from the discharge valve 11 to the nozzle 12 is preferably constructed to be as short as possible. The reason is that, during the later-described discharge operation, the shorter flow passage enables the pressure to be more quickly transmitted and enables the liquid to more easily fly and to be discharged in a stable discharge amount.

The control unit 13 is connected to the above-described two valves (6, 11) and the actuator 10, which operates the pump 9, for the purpose of controlling the operations thereof. The control unit 13 controls the opening and closing of the valves (6, 11), the speed and the stroke distance of the actuator 10, etc. Further, when the regulators (5, 7) are of the electro-pneumatic type, they are also advantageously controlled by the control unit 13. It is to be noted that, in the following description, the control unit 13 is also called a "discharge control unit" in some cases because the control unit 13 performs control regarding the discharge.

In the embodiment, in addition to the above-described components, the discharge device 1 further includes the cleaning and drying unit 14 for the purpose of, e.g., cleaning the outer surface of the tip portion of the nozzle 12. Details of the cleaning and drying unit 14 will be described below with reference to FIG. 2, etc. The cleaning and drying unit 14 is divided into a cleaning unit 16 for cleaning the outer surface of the tip portion of the nozzle 12, draining the discharge liquid 30 that remains after the cleaning, and cleaning an inner surface of the tip portion of the nozzle 12, and a drying unit 17 for drying the outer surface of the tip portion of the nozzle 12 after the cleaning.

Figure 2:
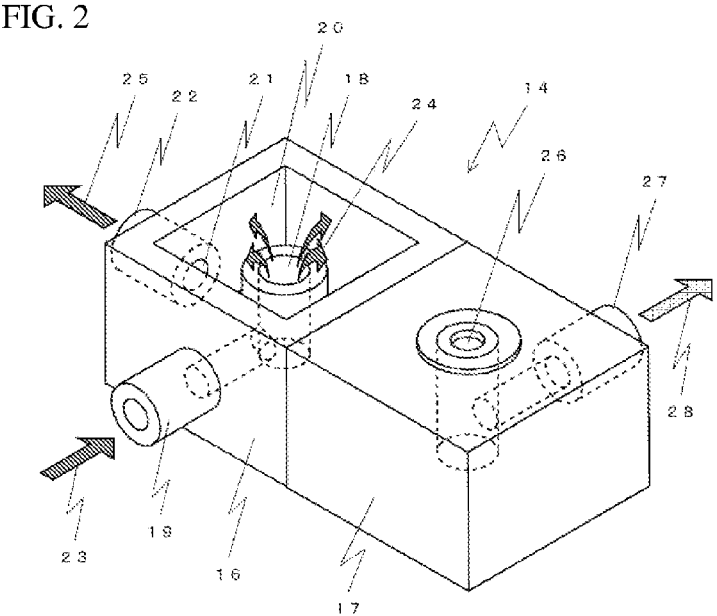
FIG. 2 is a schematic perspective view illustrating a cleaning and drying unit in the dispensing device according to the present invention.
Figure 3:
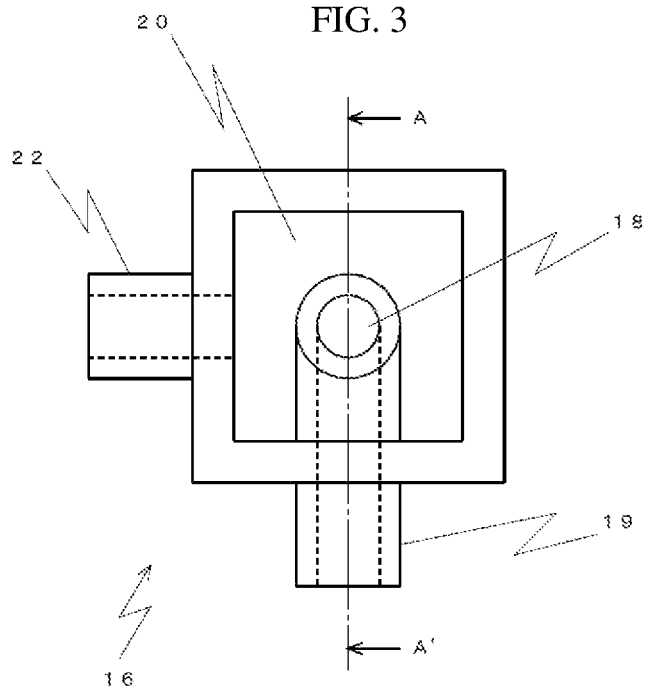
FIG. 3 is a top plan view to explain a cleaning unit in the dispensing device according to the present invention.
Figure 4:
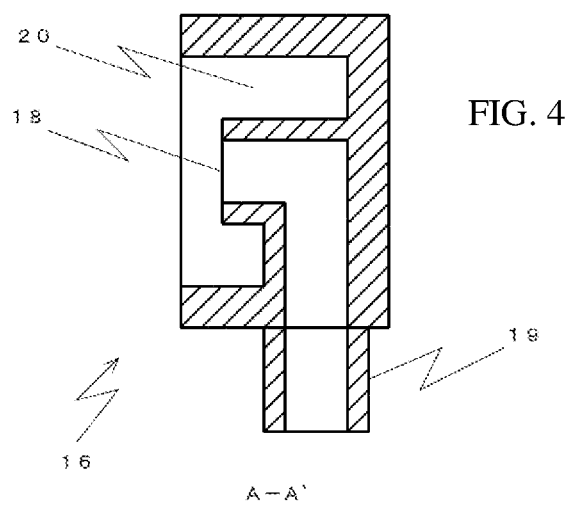
FIG. 4 is a sectional view to explain the cleaning unit in the dispensing device according to the present invention.

The cleaning unit 16 is constituted by a cleaning portion 18 and a draining portion 20. The cleaning portion 18 includes a spring-out port 18 communicating with a pipe 19 to which the cleaning liquid 2 is supplied. The cleaning liquid 2 stored in a cleaning liquid storage container 36 is supplied to the cleaning unit 16 from a direction denoted by numeral 23 in FIG. 2 with the aid of a pump 38, and is caused to spring out upwards from the spring-out port 18 (denote by numeral 24). Here, the cleaning liquid 2 is caused to spring out with the force of water comparable to that of spring water instead of the force of water forming a tall water column as in a fountain. The outer surface of the tip portion of the nozzle 12 can be cleaned by dipping the nozzle 12 in a portion of the cleaning unit 16 where the cleaning liquid 2 springs out. Because the cleaning liquid 2 continuously springs out from the spring-out port 18, washed wastes, including the discharge liquid, are prevented from flowing backward to the cleaning liquid supply side. It is to be noted that the cleaning liquid 2 is preferably the same liquid as the pressure transmission medium 2. Furthermore, as illustrated in FIG. 3, the draining portion 20 is constituted as a groove that is formed around the cleaning portion (spring-out port) 18 and that has a substantially C-shape in a top plan view. As illustrated in FIG. 4, an outer wall of a flow passage having an L-shape in section and connecting the spring-out port 18 and the pipe 19 to each other is contiguous to an inner bottom of the cleaning unit 16. A portion of the cleaning unit 16 corresponding to the flow passage having an L-shape in section is lowered by one step such that the cleaning liquid 2 will not overflow, but it is not constituted in the form of a groove unlike the draining portion 20. The cleaning liquid 2 having sprung out from the spring-out port 18 is drained from a drain port 21, which is formed through a wall of the cleaning unit 16, after passing through the groove of the draining portion 20 (in a direction of an arrow denoted by numeral 25). Furthermore, the discharge liquid 30 remaining after being dispensed is also drained through the draining portion 20. The drained cleaning liquid 2 and discharge liquid 30 flow into a waste container 37 through a pipe 22 that is connected to the drain port 21. At that time, as in the supply of the cleaning liquid 2 to the cleaning portion 18, it is preferable that the wastes are positively delivered to the outside with the aid of the pump 39.

On an upper surface of the drying unit 17, there is formed a hole having a size enough to insert the tip portion of the nozzle 12 therethrough, i.e., a hole 26 having a diameter larger than an outer diameter of the nozzle 12. The hole 26 is communicated from the inside of the drying unit 17 with a vacuum source 44 through a pipe 27 in a fluid communicating way. The hole 26 is called here an insertion hole. When the tip portion of the nozzle 12 is inserted through the insertion hole 26, air around the tip portion of the nozzle 12 is exhausted to suck the cleaning liquid 2, etc., which are attached to the outer surface of the tip portion of the nozzle 12, whereby the tip portion of the nozzle 12 is dried. In FIG. 2, an air flow is denoted by numeral 28. Moreover, a filter or the like for screening out the liquid from the sucked air is disposed between the drying unit 17 and the vacuum source 44.

Thus, since the unit 14 for performing the cleaning and the drying, along with the treatment of the wastes and the supply of the cleaning liquid 2, is disposed within a nozzle movable range, a series of operations from the cleaning to the drying of the tip portion of the nozzle 12 can be easily performed, and the series of operations can be automated. In addition, since the cleaning and the drying of the inside and the outside of the nozzle 12 can be performed together using one unit 14, it is also possible to automate the cleaning and drying operations even when plural types of discharge liquids 30 are discharged.

[Dispensing Method]

FIGS. 5 to 11 are explanatory views to explain a dispensing method according to the embodiment. Those drawings illustrate the components between the liquid regulator 5 and the nozzle 12, while the other components are omitted.

Figure 5:
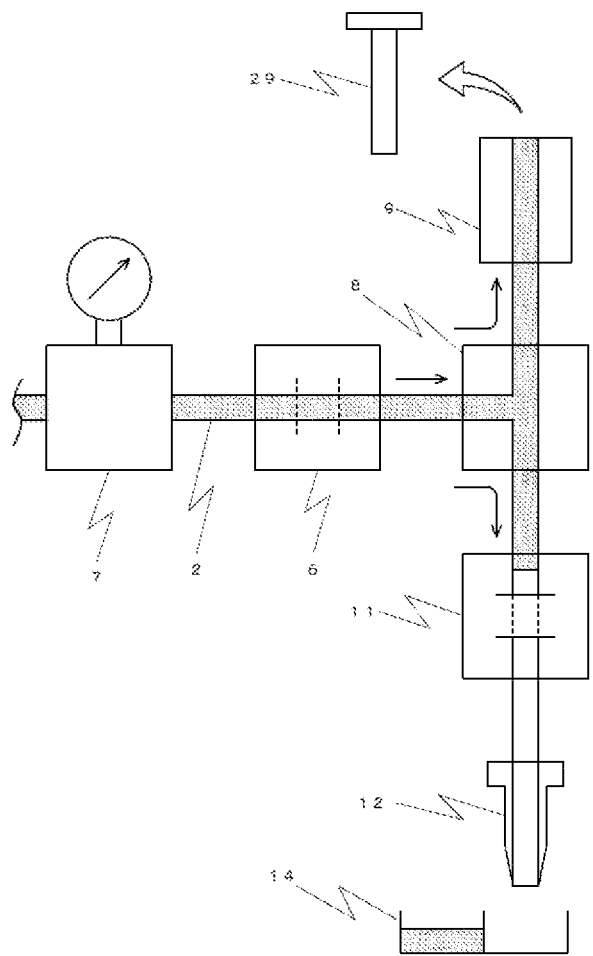
FIG. 5 is an explanatory view to explain a first half of a medium supply step in a dispensing method according to the present invention.
Figure 6:
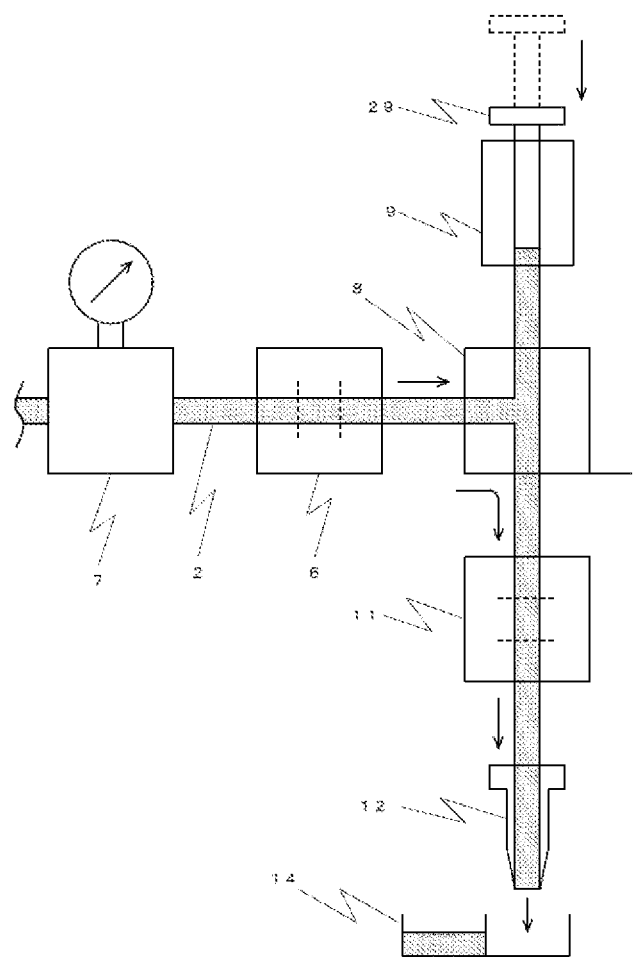
FIG. 6 is an explanatory view to explain a second half of the medium supply step in a dispensing method according to the present invention.

(1) Supply of Pressure Transmission Medium (FIGS. 5 and 6)

As a preparatory stage before starting the discharge, the pressure transmission medium 2 is filled into the flow passage (i.e., the substantially T-shaped flow passage from the supply valve 6 to the pump 9 and to the nozzle 12), which has been in an empty state.

First, of the components constituting the discharge device 1, the piston 29 of the pump 9 is dismantled, and the discharge valve 11 and the supply valve 6 are both held in the "closed" state. Next, the storage container 3 containing the pressure transmission medium 2 is connected to the inlet side of the supply valve 6, and the pressurized gas source 4 is connected to the storage container 3. At that time, the gas regulator 5 is held in a state for regulation to 0. The liquid regulator 7 is held in a state for regulation to the discharge pressure described later. Then, when the gas regulator 5 is set for regulation to a predetermined pressure, the pressure transmission medium 2 is supplied to the inlet of the supply valve 6 with the action of the pressurized gas. The setting pressure of the gas regulator 5 is preferably set to be slightly higher than the setting pressure of the liquid regulator 7, which is disposed on the downstream side, in consideration of a loss in the liquid regulator 7, etc. Thereafter, the tip portion of the nozzle 12 is moved by the XYZ moving mechanism to a position above the draining portion 20 of the cleaning unit 16 in the cleaning and drying unit 14. Then, when the supply valve 6 is brought into the "open" state, the pressure transmission medium 2 is supplied to the other side (outlet side) of the supply valve 6 with the action of the pressurized gas. More specifically, as illustrated in FIG. 5, the pressure transmission medium 2 is caused to flow in the direction toward the pump 9 while the other part of the pressure transmission medium 2 flows in the direction toward the nozzle 12. When the pressure transmission medium 2 reaches an upper end of the pump 9 or overflows the pump 9, the supply valve 6 is brought into the "closed state". The piston 29 having been dismantled is now fitted at its one end to the pump 9, and the other end of the piston is fixed to the actuator. When the discharge valve 11 and the supply valve 6 are both brought into the "open" state, the pressure transmission medium 2 is caused to flow in the direction toward the nozzle 12 and to eventually overflow from the tip end of the nozzle 12, as illustrated in FIG. 6. Upon confirming that the pressure transmission medium 2 overflows from the tip end of the nozzle 12, the supply valve 6 is brought into the "closed" state. Finally, the piston 29 is set to an "advance" position.

Operations for filling the flow passages with the pressure transmission medium 2 are thus completed.

Figure 7:
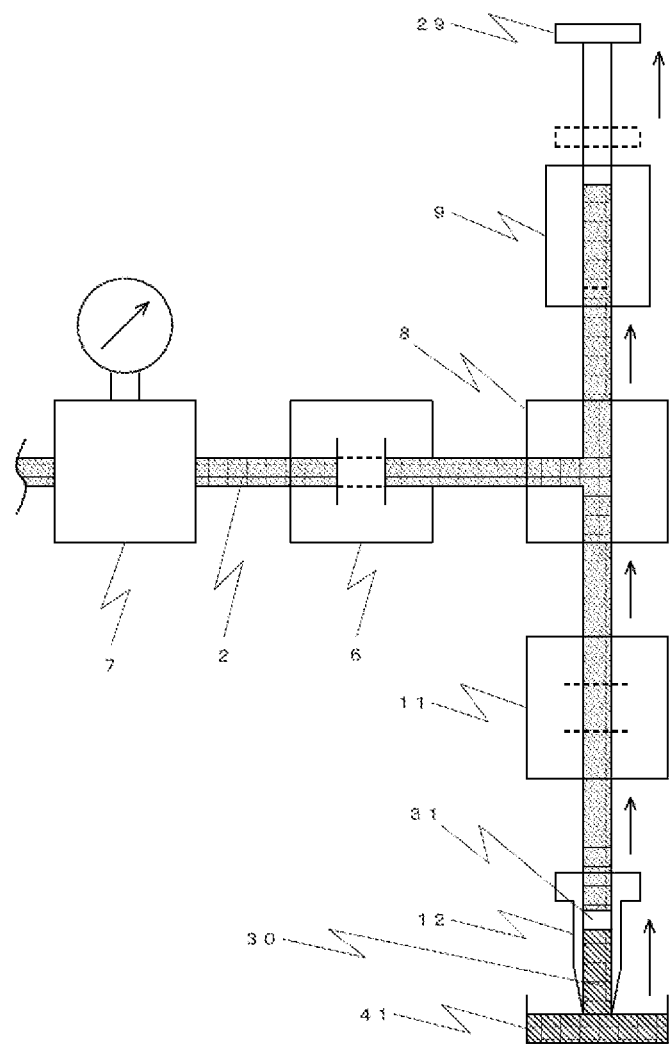
FIG. 7 is an explanatory view to explain a suction step in the dispensing method according to the present invention.

(2) Suction of Discharge Liquid (FIG. 7)

After the supply of the pressure transmission medium, an operation of sucking the discharge liquid 30 in a necessary amount, which is actually dispensed, is performed.

First, the tip portion of the nozzle 12 is moved by the XYZ moving mechanism to a position above the container 41 in which the discharge liquid 30 to be dispensed is stored. Next, before starting to suck the discharge liquid 30, the piston 29 of the pump 9 is slightly retracted with the tip end portion of the nozzle 12 held in air, thereby sucking a very small amount of air into the tip portion of the nozzle 12 to form a gap 31. The gap 31 serves to prevent mixing of the pressure transmission medium 2 and the discharge liquid 30. If the amount of sucked air is too large, the discharge amount of the discharge liquid 30 would be instable. Conversely, if the amount of sucked air is too small, mixing of the pressure transmission medium 2 and the discharge liquid 30 would occur. Therefore, the amount of sucked air is properly selected. In the embodiment, as one practical example, air is sucked in an amount corresponding to about 10% of the amount of one droplet of the discharge liquid 30. Then, the tip portion of the nozzle 12 is dipped in the discharge liquid 30 to be discharged, and the discharge liquid 30 is sucked by retracting the piston 29 of the pump 9. The amount of the sucked discharge liquid 30 is adjusted in accordance with the stroke through which the piston 29 of the pump 9 is retracted. Here, the amount of the sucked discharge liquid 30 is preferably set to be slightly larger than a total amount of the discharge liquid 30 to be dispensed. This is because, if the amount of the sucked discharge liquid and the amount of the dispensed discharge liquid are equal to each other, there is a risk that as approaching the end of the dispensing, the discharge amount becomes instable due to an influence of the air 31 having been sucked before starting to suck the discharge liquid 30, or that the discharge liquid 30 may be discharged in a randomly scattering way upon reaching a region containing the air 31 at an end of the discharge.

Here, the tip portion of the nozzle 12 is preferably set to have a length enough to store an amount of the discharge liquid 30 to be dispensed at a time (e.g., a total amount of the discharge liquid 30 to be dispensed when a plate including a plurality of recesses formed therein as an array is used and the discharge liquid 30 is dispensed into all the recesses). Furthermore, the diameter of the nozzle 12 is appropriately selected depending on the amount of one droplet to be discharged. For example, a tapered conical nozzle having a tip portion with an inner diameter of about 0.1 [mm] and a length of 5 to 10 [mm] is used in the embodiment.

Figure 8:
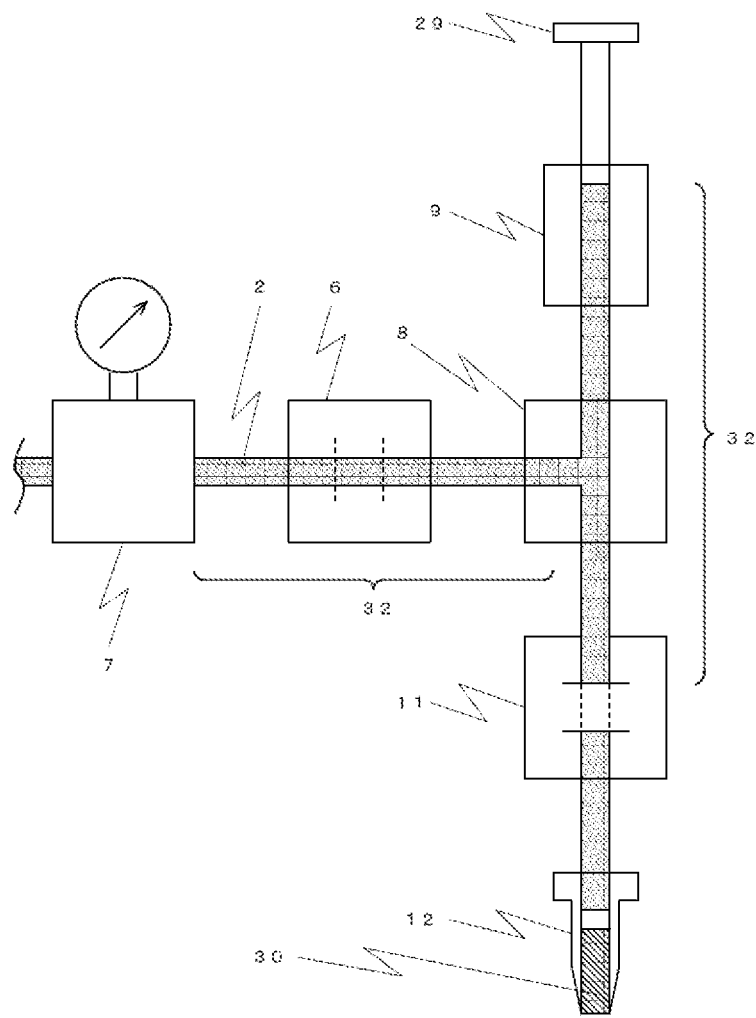
FIG. 8 is an explanatory view to explain a pressurization step in the dispensing method according to the present invention.

(3) Pressurization of Pressure Transmission Medium (FIG. 8)

After sucking the discharge liquid 30, the pressure transmission medium 2 is pressurized to the discharge pressure.

First, the discharge valve 11 is brought into the "closed" state, and the supply valve 6 is then brought into the "open" state. With that valve setting, the pressure transmission medium 2 in the flow passage from the supply valve 6 to the inlet of the discharge valve 11 is pressurized with the action of the pressurized gas. Because the liquid regulator 7 is disposed between the storage container 3 and the supply valve 6, the pressure transmission medium 2 in the flow passage from the outlet of the liquid regulator 7 to the inlet of the discharge valve 11 is pressurized to the setting pressure (=discharge pressure) of the liquid regulator 7. With the liquid regulator 7 and the above-described gas regulator 5 disposed in two stages, it is possible to not only regulate and stabilize the pressure of the pressurized gas supplied from the pressurized gas source 4 by the gas regulator 5, but also to regulate and stabilize the pressure of the pressure transmission medium 2, on which the stabilized pressurized gas acts, by the liquid regulator 7. As a result, the influences of, e.g., the water head difference in the storage container 3, the pressure variation (pulsation) in the pressurized gas source 4, and the compressibility of the gas can be removed. On other hand, the discharge liquid 30 in the flow passage from the outlet side of the discharge valve 11 to the nozzle 12 is not yet pressurized. However, since the distance from the discharge valve 11 to the nozzle 12 is set minimally short as described above, the pressure is quickly transmitted when the discharge liquid 30 is discharged. A value of the setting pressure of the liquid regulator 7 is previously determined by experiments, for example, depending on the amount of one droplet or whether the droplet is caused to fly or not. However, the value of the setting pressure of the liquid regulator 7 needs to be determined in consideration of the valve opening-closing time (described below) as well (see the following (4) for examples of concrete numeral values).

Figure 9:
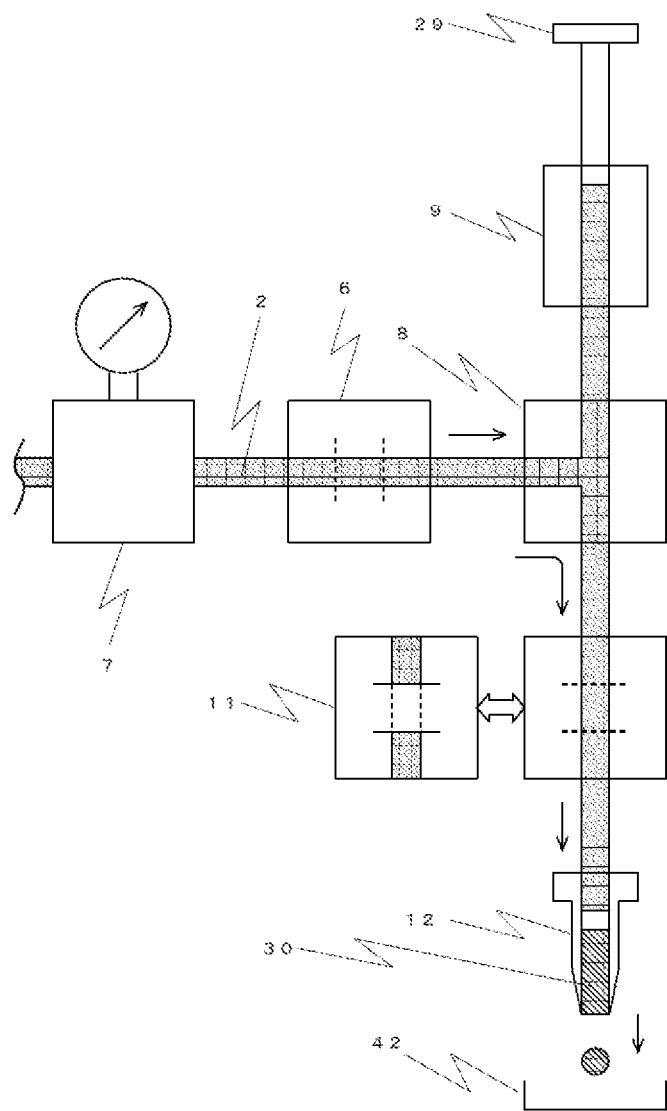
FIG. 9 is an explanatory view to explain a discharge step in the dispensing method according to the present invention.

(4) Discharge of Discharge Liquid (FIG. 9)

After the pressurization of the pressure transmission medium, the discharge is started.

First, the head unit 34 (described later) is moved by the XYZ moving mechanism such that the tip portion of the nozzle 12 is positioned above the dispensing target container 42 to which the discharge liquid 30 is to be dispensed. Then, when the discharge valve 11 is brought into the "open" state, the pressure is transmitted to the discharge liquid 30 in the nozzle 12 on the outlet side of the discharge valve 11 through the pressure transmission medium 2, whereupon the discharge liquid 30 starts to flow out from the nozzle 12. When the discharge valve 11 is brought into the "closed" state after the lapse of a predetermined time, the transmission of the pressure is stopped and the flowing-out of the discharge liquid 30 from the nozzle 12 is also stopped. By applying a higher pressure than that when the liquid is discharged with the action of the piston 29 of the pump 9 and by opening and closing the discharge valve 11 at a high speed, the discharge liquid 30 can be caused to fly in the form of a droplet from the nozzle 12 and can be discharged to a dispensing position of the dispensing target container 42. Further, the discharge method utilizing the action of the pressure applied from the pressurized gas source 4 enables the fly discharge to be performed in a very small amount of one droplet, which is difficult to realize with the discharge method utilizing the action of the piston 29. When the dispensing target container 42 has a plurality of dispensing positions, the above-described movement of the nozzle 12 and the above-described opening and closing of the discharge valve 11 are repeated. As with the pressure value, a value of the setting time is also previously determined by experiments, for example, depending on the amount of one droplet or whether the droplet is caused to fly or not. Here, the discharge amount is adjusted mainly based on the valve opening-closing time. In other words, the pressure setting is hardly changed once determined. One reason is that time response is superior to pressure response. Another reason is that, because the time is substantially proportional to the discharge amount, adjustment of the setting is relatively easy. In a practical example, a liquid of about 60 [nL] (nano-liter) is discharged by applying a pressure of 30 [kPa] (kilo-Pascal) to the discharge liquid with viscosity of about 1 [mPa·s] (milli-Pascal second) and by opening and closing the discharge valve at an interval of 1 [msec] (millisecond). A liquid of about 120 [nL] (nano-liter) is discharged by applying the same pressure to the same discharge liquid for the valve opening-closing time of 2 [msec] (millisecond).

Figure 10:
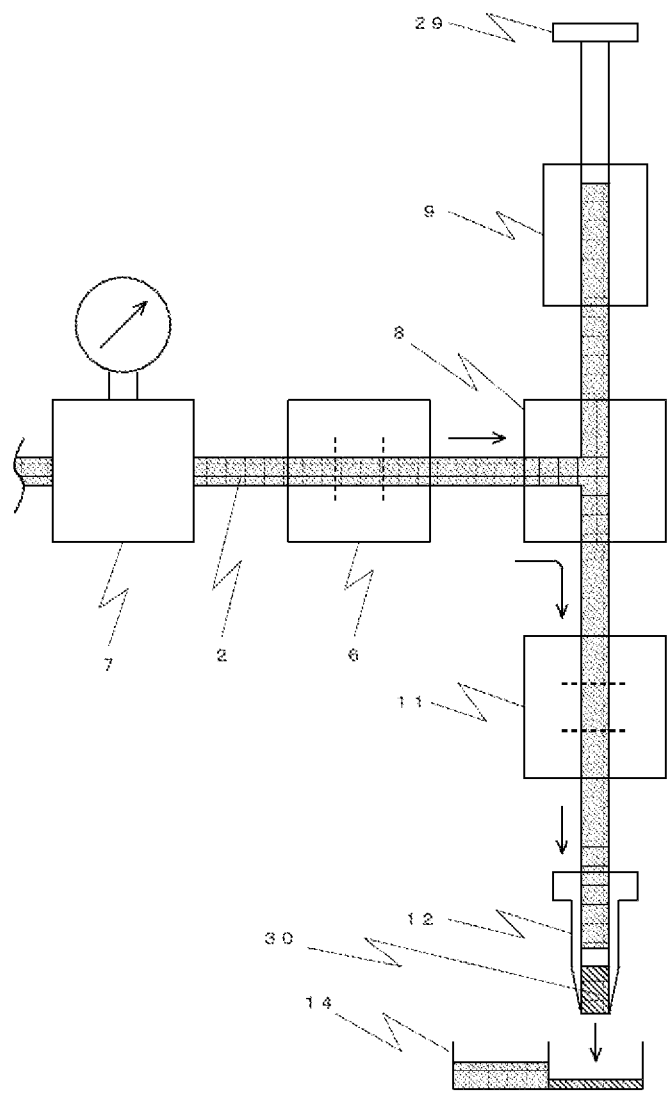
FIG. 10 is an explanatory view to explain draining, cleaning and drying steps in the dispensing method according to the present invention.

(5) Draining, Cleaning and Drying (FIG. 10)

When the liquid discharge to all the dispensing positions of the dispensing target container 42 has been completed, or when a different type of discharge liquid 30 is to be discharged, the discharge liquid 30 remaining in the nozzle 12 is drained and, at the same time, the inside and the outside of the nozzle 12 are cleaned.

First, the discharge valve 11 is brought into the "closed" state, and the head unit 34 (described later) is moved by the XYZ moving mechanism such that the tip portion of the nozzle 12 is positioned above the draining portion 20 of the cleaning unit 16 in the cleaning and drying unit 14. Then, the discharge valve 11 is brought into the "open" state to drain the discharge liquid 30 remaining in the nozzle 12. At that time, the discharge liquid 30 in the nozzle 12 is drained together with the pressure transmission medium 2 by pressing the discharge liquid 30 with the pressure transmission medium 2. This enables the inner surface of the tip portion of the nozzle 12 to be cleaned with the pressure transmission medium 2 that serves also as the cleaning liquid 2. Furthermore, a draining step is preferably performed after moving the nozzle 12 by the XYZ moving mechanism to be positioned below an upper end of the wall of the draining portion 20 of the cleaning unit 14, so that the wastes are not scattered to the surroundings. After the draining, the discharge valve 11 is brought into the "closed" state. Next, the tip portion of the nozzle 12 is moved by the XYZ moving mechanism to a position above the cleaning portion 18 of the cleaning unit 16 in the cleaning and drying unit 14, and the outer surface of the nozzle 12 is cleaned with the cleaning liquid 2 that is springing out from the cleaning portion 18. When cleaning the nozzle 12, the nozzle 12 is just required to be dipped in the cleaning liquid 2 springing out upward of the spring-out port 18 instead of inserting the nozzle 12 into the spring-out port 18. When a cleaning region of the nozzle 12 is to be changed, it is just necessary to change the springing-out force of the cleaning liquid 2. The cleaning liquid 2 used here is preferably the same as the pressure transmission medium 2. The reason is that, if the cleaning liquid 2 and the pressure transmission medium 2 are different from each other, mixing of the cleaning liquid 2 and the pressure transmission medium 2 occurs in a region of the tip portion of the nozzle 12 where the tip portion is dipped in the cleaning liquid 2.

Subsequently, the tip portion of the nozzle 12 is moved by the XYZ moving mechanism to a position above the drying unit 17 in the cleaning and drying unit 14, and the tip portion of the nozzle 12 is inserted into the insertion hole 26. The tip portion of the nozzle 12 is then dried by sucking air around the nozzle 12 and attracting an extra liquid (mainly the cleaning liquid 2) that is attached to the outer surface of the nozzle 12. By thus drying the tip portion of the nozzle 12 without leaving the cleaning liquid 2, etc. in a state attached to the outer surface of the tip portion of the nozzle 12, the mixing of the cleaning liquid 2 and the discharge liquid 30 can be reliably avoided when the discharge liquid 30 is sucked in a next cycle.

Figure 11:
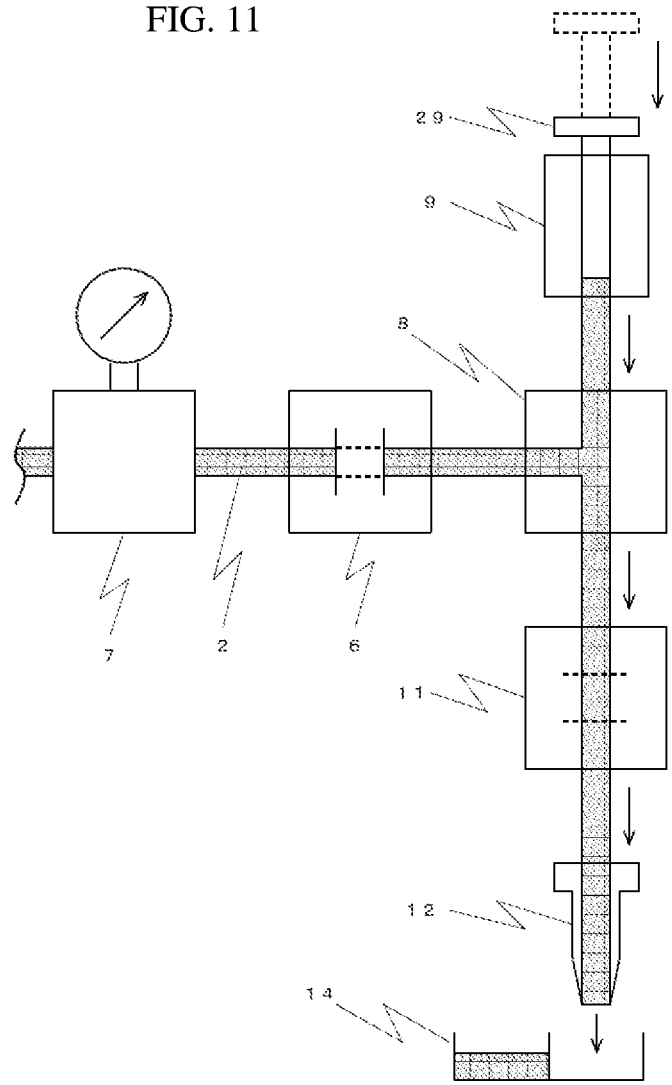
FIG. 11 is an explanatory view to explain an initialization step in the dispensing method according to the present invention.

(6) Initialization (FIG. 11)

After the draining, cleaning, and drying steps, operations of removing the pressure applied so far and returning to the initial state are performed to be preparatory for starting the suction in the next cycle.

First, the tip portion of the nozzle 12 is moved by the XYZ moving mechanism to a position above the draining portion 20 of the cleaning unit 16 in the cleaning and drying unit 14, the supply valve 6 is brought into the "closed" state, and the discharge valve 11 is brought into the "open" state. With that valve setting, the supply of the pressure transmission medium 2 is stopped, thus resulting in a state where the pressure in the flow passage from the outlet of the supply valve 6 to the nozzle 12 is removed (pressure=0, atmospheric pressure). The piston 29 of the pump 9 is then advanced into a state capable of sucking the discharge liquid 30 through the discharge port of the nozzle 12. At that time, the pressure transmission medium 2 is drained into the draining portion 20 of the cleaning unit 16 through the nozzle 12 in an amount corresponding to the advance of the piston 29. At the end of those operations, the same state as the final state in above (1) is obtained, and the dispensing device is set to be preparatory for starting next operations at any time.

When discharging different types of the discharge liquids 30, the above-described operations of (2) to (6) are repeated each time the type of the discharge liquid 30 is changed. When the amount of the discharge liquid 30 sucked in one sucking step is insufficient for the same type of discharge liquid 30, it is also preferable to repeat the above-described operations of (2) to (6). The reason is that the piston 29 of the pump 9 has to be descended in the sucking step.

According to the present invention, as described above, since the liquid regulator 7 and the gas regulator 5 are disposed in two stages for pressure adjustment, it is possible to not only regulate and stabilize the pressure of the pressurized gas supplied from the pressurized gas source 4 by the gas regulator 5, but also to regulate and stabilize the pressure of the pressure transmission medium 2, on which the stabilized pressurized gas acts, by the liquid regulator 7. As a result, the influences of, e.g., the water head difference in the storage container 3, the pressure variation (pulsation) in the pressurized gas source 4, and the compressibility of the gas can be removed. Furthermore, since the liquid regulator 7 is disposed upstream of the inlet of the supply valve 6, the pressure transmission medium 2 under the regulated and stabilized pressure can be supplied to the supply valve 6 and the other components connected to the outlet side thereof, which are related to the liquid discharge. Hence accuracy and stability in the liquid discharge can be increased.

Moreover, since the unit 14 for performing the cleaning and the drying, along with the treatment of the wastes and the supply of the cleaning liquid, is disposed within a nozzle movable range, a series of operations from the cleaning to the drying of the tip portion of the nozzle 12 can be quickly and easily performed, and the series of operations can be automated. Since the tip portion of the nozzle 12 is dried without leaving the cleaning liquid, etc. in a state attached to the outer surface of the tip portion of the nozzle 12, the mixing of the cleaning liquid and the discharge liquid can be reliably avoided when the discharge liquid is sucked in a next cycle. In addition, since the cleaning and the drying of the inside and the outside of the nozzle 12 can be performed together using one unit 14, it is also possible to automate the cleaning and drying operations even when plural types of discharge liquids 30 are discharged.

Since a higher pressure than that obtained with the action of the piston 29 of the pump 9 can be applied and the discharge valve 11 can be opened and closed at a high speed, the discharge liquid 30 can be caused to fly in the form of a droplet from the nozzle 12 for discharge to a target. Additionally, since the discharge method is based on the action of pressure, it is possible to perform the fly discharge in a very small amount of one droplet, which is difficult to realize with the discharge method utilizing the action of the piston 29.

Details of the present invention will be described below in connection with Example, but the present invention is in no way restricted by the following Example.

EXAMPLE

[Entire Construction]

Figure 12:
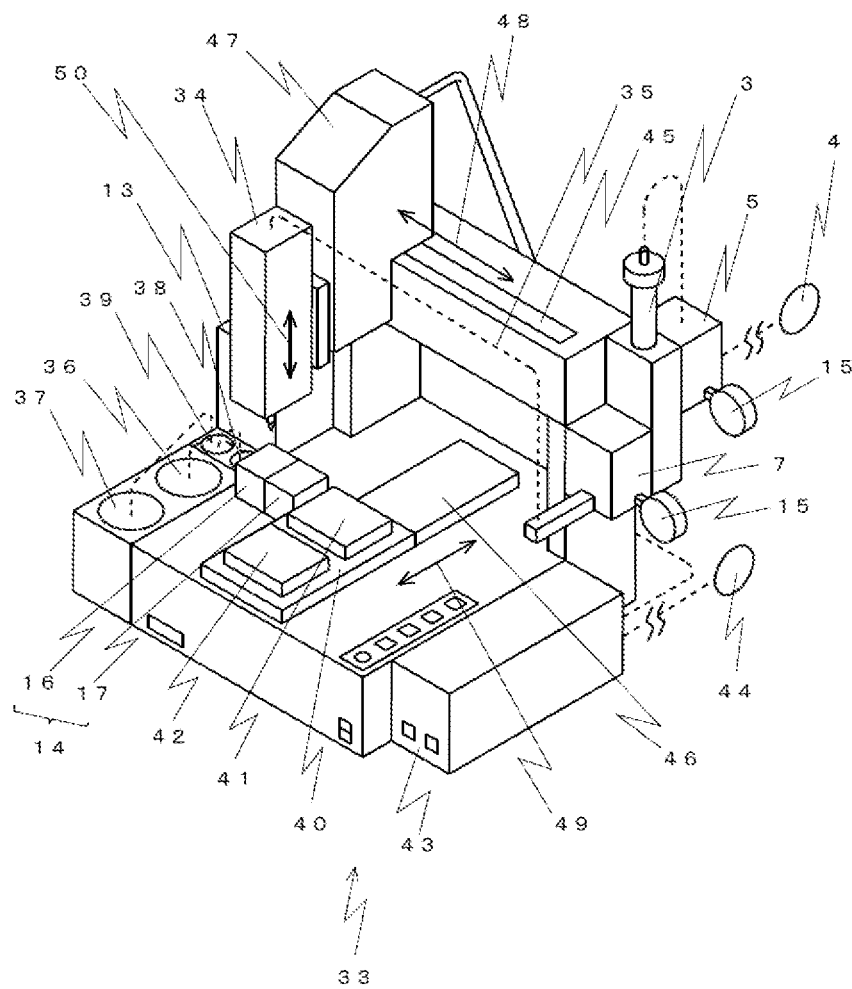
FIG. 12 is a schematic perspective view illustrating an overall construction of the dispensing device according to the present invention.

FIG. 12 illustrates an overall construction of a dispensing device according to Example.

A dispensing device 33 according to this Example includes, as main components, the discharge device 1 for, e.g., sucking and discharging the discharge liquid 30 and cleaning the nozzle 12, a work table 40 on which the dispensing target container 42 and the discharge liquid container 41 are placed, and the XYZ mechanism for moving the nozzle 12 and the work table 40 relatively to each other. Those components are described in detail below.

(1) Discharge Device

The discharge device 1 has basically the same construction as that illustrated in FIG. 1, but individual constituent units are disposed in different positions.

First, the nozzle 12, the branch block 8, the pump 9, the actuator 10, and the supply valve 6 are mounted integrally with one base, and the base is mounted to a Z moving mechanism 47 (described later). A group of those components collectively mounted to the base is called the head unit 34 (surrounded by the dotted line in FIG. 1). The head unit 34 is covered with a cover except for the nozzle 12.

Next, the liquid regulator 7, the storage container 3, and the gas regulator 5 are mounted laterally of a housing of the dispensing device 33. The reason why the regulators (5, 7) and the storage container 3 are mounted separately from the head unit 34 is as follows. If the regulators (5, 7) and the storage container 3 are also included in the head unit 34, the weight and the size of the head unit 34 are so increased as to cause an adverse influence on, e.g., positioning accuracy and durability of the XYZ moving mechanism. The storage container 3 is just required to be an enclosed container as described in the embodiment, and the material, shape, etc. of the storage container 3 may be optionally selected. For example, a tank, a bottle, or a syringe used in an air type dispenser may be used as the storage container 3. While FIG. 12 illustrates an analog type as the gauge (pressure gauge) 15 associated with each regulator (5, 7), it is a matter of course that a digital type may also be used instead. Furthermore, as described in the embodiment, a dispense controller may be used instead of the gas regulator.

The supply valve 6 in the head unit 34 and the liquid regulator 7 are connected to each other through a piping line 35 denoted by a dotted line. The piping line 35 is preferably made of a flexible material in consideration of the movement of the head unit 34.

The pressurized gas source 4 is disposed separately from the dispensing device 33 and is connected to the gas regulator 5 through a piping line. The pressurized gas source 4 is illustrated here in a simplified form. In a practical example disclosed here, the pressurized gas source 4 is constituted by employing a general compressor or by receiving a pressurized gas directly supplied from factory equipment.

The cleaning and drying unit 14 is mounted on an upper surface of the housing laterally of the work table 40 at a position not interfering with the table movement. The cleaning and drying unit 14 has the same construction as that illustrated in FIG. 2, and it includes the cleaning unit 16 and the drying unit 17. The cleaning liquid container 36, the waste container 37, the cleaning liquid pump 38, and the waste pump 39, which are all associated with the cleaning unit 16, are mounted laterally of a body of the dispensing device 33, i.e., laterally of the housing on the side opposite to the regulators (5, 7), at a position adjacent to the cleaning and drying unit 14.

The cleaning unit 16 is connected to the cleaning liquid container 36 and to the waste container 37 by piping lines via the cleaning liquid pump 38 and the waste pump 39, respectively. There are two piping lines, i.e., one for delivering the cleaning liquid 2 from the cleaning liquid container 36 to the cleaning portion 18 by the cleaning liquid pump 38, and the other for delivering the wastes, which are drained from the draining portion 20, to the waste container 37 by the waste pump 39.

The discharge control unit 13 is mounted laterally of the housing of the dispensing device 33 on the same side as the cleaning and drying unit 14. The discharge control unit 13 controls the operations of the actuator 10 for actuating the pump 9, and the operations of the two valves (6, 11). The discharge control unit 13 further controls the operations of the cleaning liquid pump 38 and the waste pump 39, which are included the cleaning unit 16.

(2) Work Table

The discharge liquid container 41 and the dispensing target container 42 are placed on an upper surface of the work table 40. In this Example, those containers (41, 42) are each a plate-like member including a plurality of wells (recesses) formed in an array, and plural types of samples, reagents and/or specimens are put in the plural wells. Analysis and inspection are performed by sucking the samples and/or the reagents in the wells, or by discharging the samples and/or the reagents to the wells.

The containers (41, 42) can be each fixedly held, for example, by a method of boring a plurality of holes extending from the inside of the table 40 to an upper surface thereof and sucking air from the holes, thereby fixedly holding the container in place under suction, or a method of gripping the container with fixing members and securing the fixing members to the table 40 with securing means, e.g., screws, thereby fixedly holding the container in place. In the case of fixedly holding the container under suction, a vacuum source 44 needs to be separately connected to the container. It is also needed to control turning-on/off of the suction. The suction fixing is preferably employed in consideration of convenience in handling. This Example represents the case of the suction fixing. A vacuum control unit 43 for controlling a negative-pressure gas, which is used for the suction in the drying unit 17 and for the suction fixing to the work table 40, is mounted laterally of the housing of the dispensing device 33. The vacuum source 44 is disposed separately from the dispensing device 33 and is connected to the vacuum control unit 43 through a piping line.

While the containers (41, 42) may be each mounted at a position not interfering with the movement of the work table 40 like the cleaning and drying unit 14, they are preferably mounted together on the work table 40 when there is a sufficient space on the work table 40. The reason is that such an arrangement is effective in shortening the distance necessary for moving between the discharge liquid container 41 and the dispensing target container 42, and hence cutting the operating time.

(3) XYZ Moving Mechanism

The XYZ moving mechanism is mounted on a gate type frame, and it includes an X moving mechanism 45 for moving a Z moving mechanism 47, on which the head unit 34 is mounted, in a direction denoted by numeral 48, a Y moving mechanism 46 mounted below the X moving mechanism 45 and moving the work table 40 in a direction denoted by numeral 49, and the Z moving mechanism 47 mounted on the X moving mechanism 45 and moving the head unit 34 in a direction denoted by numeral 50.

A control unit (not illustrated) for those moving mechanisms is installed within the housing below the Y moving mechanism 46. The control unit controls the XYZ moving operations and further transmits an operation signal to the discharge control unit 13 that controls the discharge device 1. In addition, there is provided a storage unit (not illustrated) for storing a coating program, which is prepared in the routine form to control the XYZ moving operations, the timing of the discharge operation, etc.

[Dispensing Operation]

A series of operations performed by the dispensing device 33 will be described in brief. Basic operations are substantially the same as those described above in the embodiment. The discharge liquids used in this Example are bloods, urines, and reagents for detecting antigens and antibodies from them, and are dispensed in units of a dispense amount of 20 to 30 mL (nano-liter) to a microplate in which a number 96 (8×12) of wells are formed.

First, the discharge liquid container 41 and the dispensing target container 42 are placed on and fixed to the work table 40. Further, the storage container 3 containing the pressure transmission medium 2, the cleaning liquid container 36, and the waste container 37 are mounted, and piping lines are connected to the pumps (38, 39), the head unit 34, etc.

Then, the supply of the pressure transmission medium 2 and the suction and the pressurization of the discharge liquid 30 are performed in accordance with the procedures illustrated in FIGS. 5 to 11, which have been described above in the embodiment.

Then, the head unit 34 is moved to the dispensing target container 42, and the discharge liquid 30 is discharged (see FIG. 9). At that time, when the discharge liquid 30 is continuously discharged to a plurality of wells, the discharge is preferably performed while moving the head unit 34 without stopping the head unit 34 whenever it is moved to a position above each well, from the viewpoint of cutting the operating time.

When a different type of discharge liquid 30 is to be discharged midway the dispensing operation, the tip portion of the nozzle 12 containing the discharge liquid 30 of which dispensing has finished is subjected to the draining, the cleaning and the drying in accordance with the draining, cleaning and drying procedures described above in the embodiment, and a new type of discharge liquid 30 is sucked and discharged (see FIGS. 10 and 11). When still another type of discharge liquid 30 is to be discharged, the above-described draining, cleaning, drying, sucking and discharging steps are repeated. When ending the operations, it is preferable to finish the entire operation after the end of the draining, cleaning and drying steps.

By employing the dispensing device 33 automated as described above, a lot of operations can be performed at a high speed, which operations are difficult for a person to manually perform using a pipette, for example. It has been confirmed that the dispensing device 33 of Example 1 can realize high dispensing accuracy with a variation of the discharge amount in the range of about 1 to 0.5%.

LIST OF REFERENCE SYMBOLS

1 discharge device/2 pressure transmission medium, cleaning liquid/3 storage container/4 pressurized gas source/5 gas regulator/6 supply valve/7 liquid regulator/8 branch block/9 pump/10 actuator/11 discharge valve/12 nozzle/13 discharge control unit/14 cleaning and drying unit/15 gauge (pressure gauge)/16 cleaning unit/17 drying unit/18 cleaning portion, spring-out port/19 cleaning liquid supply pipe/20 draining portion/21 drain port/22 waste delivery pipe/23 direction in which cleaning liquid flows in/24 direction in which cleaning liquid springs out/25 direction in which wastes flow out/26 insertion hole/27 suction air outflow pipe/28 direction in which suction air flows out/29 piston/30 discharge liquid (liquid sample, liquid reagent)/31 gap (mixing prevention air)/32 pressurization region/33 dispensing device/34 head unit/35 piping line (between the supply valve and the liquid regulator)/36 cleaning liquid container/37 waste container/38 cleaning liquid pump/39 waste pump/40 work table/41 discharge liquid container/42 dispensing target container/43 vacuum control unit/44 vacuum source/45 X moving mechanism/46 Y moving mechanism/47 Z moving mechanism/48 X moving direction/49 Y moving direction/50 Z moving mechanism

The invention claimed is:

1. A discharge device for sucking a discharge liquid in an amount corresponding to plural discharges through a discharge port of a nozzle unit having a flow passage, which is filled with a pressure transmission medium, with a gap interposed between the pressure transmission medium and the discharge liquid, and for continuously fly-discharging very small amounts of liquid droplets, the discharge device comprising:
   the nozzle unit having the flow passage that is communicated with the discharge port;
   a storage unit comprising a storage container and a liquid regulator, the storage unit supplying the pressure transmission medium in liquid phase under regulated pressure to the flow passage of the nozzle unit;
   a pressurization unit comprising a pressurized gas source, the pressurization unit supplying a pressurized gas under regulated pressure to the storage unit;
   a pump mechanism communicated with the storage unit and the nozzle unit in a fluid communicating way;
   a branch unit provided with a branched flow passage for communicating the nozzle unit, the storage unit, and the pump mechanism with each other;
   a discharge valve for establishing or blocking communication between the branch unit and the nozzle unit;
   a supply valve for establishing or blocking communication between the branch unit and the storage unit; and
   a control unit,
   wherein the control unit performs control such that, in a state where the discharge valve is closed and the supply valve is opened, the pressurized gas under pressure regulated by the pressurization unit is supplied to the storage container and the pressure transmission medium in liquid phase under pressure regulated by the storage unit is supplied to the flow passage of the nozzle unit, and that the discharge valve is then opened and closed at predetermined timings, thereby continuously fly-discharging the very small amounts of liquid droplets.

2. The discharge device according to claim 1, wherein the pressurization unit includes a gas regulator.

3. The discharge device according to claim 1, wherein the pressurization unit includes a dispense controller.

4. The discharge device according to claim 1, wherein the branch unit is constituted as a block-like member, and the discharge device includes a head unit that is constituted by arranging the block-like member, the supply valve, the pump mechanism, the discharge valve, and the nozzle unit integrally with one base.

5. A liquid dispensing device comprising the discharge device according to claim 1, a work table on which a dispensing target container and a discharge liquid container are placed, and an XYZ moving mechanism for moving the nozzle unit and the work table relatively to each other.

6. The liquid dispensing device according to claim 5, further comprising a cleaning unit that includes a draining portion for receiving the liquid discharged from the nozzle unit and a cleaning liquid spring-out port, and a drying unit for causing a suction force to act on a tip portion of the nozzle unit, thereby drying the tip portion of the nozzle unit.

7. The liquid dispensing device according to claim 5, wherein the liquid dispensing device is a desktop type.

8. A liquid dispensing method for continuously discharging a discharge liquid by employing a liquid dispensing device, which comprises a nozzle unit having a flow passage that is communicated with a discharge port, a storage unit comprising a storage container and a liquid regulator, the storage unit supplying a pressure transmission medium in liquid phase under regulated pressure to the nozzle unit, a pressurization unit having a pressurized gas source, the pressurization unit supplying a pressurized gas under regulated pressure to the storage container, a pump mechanism communicated with the storage unit and the nozzle unit in a fluid communicating way, a branch unit provided with a branched flow passage for communicating the nozzle unit, the storage unit, and the pump mechanism with each other, a discharge valve for establishing or blocking communication between the branch unit and the nozzle unit, a supply valve for establishing or blocking communication between the branch unit and the storage unit, a work table on which a dispensing target container and a discharge liquid container are placed, and an XYZ moving drive for moving the nozzle unit and the work table relatively to each other, the liquid dispensing method comprising:
   a first step of sucking the discharge liquid in an amount corresponding to plural discharges through the discharge port of the nozzle unit having the flow passage, which is filled with the pressure transmission medium, with a gap interposed between the pressure transmission medium and the discharge liquid;
   a second step of supplying the pressurized gas to the storage unit in a state where the discharge valve is closed and the supply valve is opened, and supplying the pressure transmission medium in liquid phase under pressure regulated by the storage unit to the nozzle unit; and a third step of opening and closing the discharge valve at predetermined timings while moving the nozzle unit and the work table relatively to each other, thereby continuously fly-discharging very small amounts of liquid droplets.

9. A liquid dispensing method for continuously discharging plural types of discharge liquids by employing a liquid dispensing device, which comprises a nozzle unit having a flow passage that is communicated with a discharge port, a storage unit having storage container and a liquid regulator, the storage unit supplying a pressure transmission medium in liquid phase under regulated pressure to the nozzle unit, a pressurization unit having a pressurized gas source, the pressurization unit supplying a pressurized gas under regulated pressure to the storage container, a pump mechanism communicated with the storage unit and the nozzle unit in a fluid communicating way, a branch unit provided with a branched flow passage for communicating the nozzle unit, the storage unit, and the pump mechanism with each other, a discharge valve for establishing or blocking communication between the branch unit and the nozzle unit, a supply valve for establishing or blocking communication between the branch unit and the storage unit, a work table on which a dispensing target container and a discharge liquid container are placed, an XYZ moving drive for moving the nozzle unit and the work table relatively to each other, a cleaning unit that includes a draining portion for receiving the liquid discharged from the nozzle unit and a cleaning liquid spring-out port, and a drying unit for causing a suction force to act on a tip portion of the nozzle unit, thereby drying the tip portion of the nozzle unit, the liquid dispensing method comprising:
- a first step of sucking the discharge liquid in an amount corresponding to plural discharges through the discharge port of the nozzle unit having the flow passage, which is filled with the pressure transmission medium, with a gap interposed between the pressure transmission medium and the discharge liquid;
- a second step of supplying the pressurized gas to the storage unit in a state where the discharge valve is closed and the supply valve is opened, the pressurized gas, and supplying the pressure transmission medium in liquid phase under pressure regulated by the storage unit to the nozzle unit;
- a third step of continuously fly-discharging very small amounts of liquid droplets by opening and closing the discharge valve at predetermined timings while moving the nozzle unit and the work table relatively to each other;
- a fourth step of moving the nozzle unit to the cleaning unit, draining the discharge liquid remaining in the nozzle unit, and cleaning the tip portion of the nozzle unit;
- a fifth step of moving the nozzle unit to the drying unit and drying the tip portion of the nozzle unit;
- a sixth step of moving the nozzle unit to the cleaning unit and draining the pressure transmission medium through the discharge port in a state where the supply valve is closed and the discharge valve is opened; and
- a seventh step of performing the first to third steps for a second discharge liquid.

10. The liquid dispensing method according to claim 8, wherein an amount of the droplet discharged at a time is 1 µL or less.

11. The liquid dispensing method according to claim 10, wherein the amount of the droplet discharged at a time is several tens nL or less.

12. The discharge device according to claim 1, wherein an amount of each of the continuously fly-discharged droplets is adjusted by adjusting an opening-closing time of the discharge valve.

13. The liquid dispensing method according to claim 8, wherein, in the third step of, an amount of each of the continuously fly-discharged droplets is adjusted by adjusting an opening-closing time of the discharge valve.

14. The liquid dispensing method according to claim 8, wherein the pressurization unit includes a gas regulator or a dispense controller, and
- in the second step, the pressurized gas under a certain pressure regulated by the pressurization unit is supplied to the storage unit side.

* * * * *